United States Patent [19]
Sherman et al.

[11] Patent Number: 6,096,711
[45] Date of Patent: Aug. 1, 2000

[54] HSP72 INDUCTION AND APPLICATIONS

[76] Inventors: Michael Sherman, 581 Saw Mill Brook Pkwy., Newton, Mass. 02159; Anatoli Meriin, 64 Brighton Ave., #211, Allston, Mass. 02134; Vladimir Gabai, 75 Park St., #5; Vladimir Volloch, 358 Tappen St., both of Brookline, Mass. 02146

[21] Appl. No.: 09/030,297

[22] Filed: Feb. 25, 1998

[51] Int. Cl.$^7$ .................................................. A61K 38/00
[52] U.S. Cl. .................................. 514/18; 514/2; 514/17; 514/19; 436/63; 436/86; 436/536; 436/173; 436/179
[58] Field of Search ................................ 514/2, 17, 18, 514/19; 436/63, 86, 536, 173, 179

[56] References Cited

U.S. PATENT DOCUMENTS

| | | | |
|---|---|---|---|
| 5,550,262 | 8/1996 | Iqbal et al. | 554/57 |
| 5,580,854 | 12/1996 | Orlowski et al. | 514/18 |
| 5,614,649 | 3/1997 | Iqbal et al. | |
| 5,693,617 | 12/1997 | Stein et al. | |
| 5,942,494 | 8/1999 | Ginsberg et al. | 514/18 |

OTHER PUBLICATIONS

Zhou et al., The Journal of Biol. Chem. vol. 271, No. 40, pp. 24769–24775, 1996.
Rudinger, Peptide Hormones, University Park Press, pp. 1–7, 1976.
Gabai et al., *J. of Biol. Chem.* 272: 18033–18037 (1997).
Sistonen et al., *Mol. Cell. Biol.* 14: 2087–2099 (1994).
Nakai et al., *Mol. Cell. Biology* 15: 5268–5278 (1995).
Zhou et al., *J. of Biol. Chem.* 271: 24769–24775 (1996).
Morimoto et al., *Stress–Inducible Cellular Responses* (Feige et al., ed)^eds) 77: 139–163, Birkhauser Verlag, Basel (1996).
Voellmy, R., *Stress–Inducible Cellular Responses* (Feige et al., ed)^eds) 77: 121–137, Birkhauser Verlag, Basel (1996).
Tanabe et al., *J. of Biol. Chem.* 272: 15389–15395 (1997).
Simon et al., *J. Clin. Invest.* 95: 926–933 (1995).
Samali et al., *Exp. Cell Res.* 223: 163–170 (1996).
Gabai et al., *FEBS Lett* 375: 21–26 (1995).
Mosser et al., *J. Cell Physiol.* 151: 561–570 (1992).

*Primary Examiner*—Dwayne C. Jones
*Assistant Examiner*—C. Delacroix-Muirheid

[57] ABSTRACT

Disclosed herein is a method for inducing Hsp72 production in a cell. The method involves contacting the cell transiently with a proteasome inhibitor in an amount sufficient to induce Hsp72 production. Preferably Hsp72 levels are induced to a level sufficient for the suppression of stress-activated kinase activity attributable, for example, to a stress-activated kinase selected from the group consisting of JNK and p38. The method has both in vitro and in vivo applications. Also disclosed is a method of the type described above is applied specifically to aged cells. Also disclosed is a method for treating pathologies associated with apoptosis and inflammation in an individual. The method involves administering to the individual a proteasome inhibitor in an amount sufficient to induce Hsp72 production. In a preferred embodiment of the therapeutic method, the individual is an aged individual. Stress-induced pathologies such as ischemia are particularly important with respect to the therapeutic aspect of the invention. Also disclosed is a method for identifying an organic compound having the ability to induce Hsp72 levels in aged cells to a level sufficient to suppress stress-activated kinase activity.

21 Claims, No Drawings

HSP72 INDUCTION AND APPLICATIONS

BACKGROUND OF THE INVENTION

In all living organisms, heat shock and other stresses cause induction of a group of heat shock proteins (Hsps), which play an important role in protection of cells against adverse effects of stresses. The age-related attenuation of inducibility of Hsps correlates with the increase in morbidity and mortality of aged organisms exposed to hyperthermia. For example, the rate of heat stroke is more than 10-fold higher for persons of 65 years or older as compared to younger individuals. This suggests that basic physiological changes in the organism, rather than underlying diseases, may be responsible for the age-related increase in heat stroke. Diminishing inducibility of Hsps and increasing sensitivity to heat shock with aging has also been observed in cell cultures. Indeed, cells isolated from the aged organisms, as well as cells isolated from young organisms and aged in culture, show reduced ability to induce Hsps upon stress and increased stress-sensitivity. Therefore, elucidating molecular events underlying age-related sensitivity to stress at the cellular level would help to understand responses to stresses by aged organisms.

Over the past years, a number of studies have shown that the major heat-inducible protein, Hsp72, is critical for protection of cells and tissues from heat shock and other stresses. Hsp72 functions as molecular chaperone in refolding and degradation of damaged proteins. This has led to the common assumption that chaperoning activities of Hsp72 determine its role in ability of a cell to protect itself against stresses. Upon exposure to stresses that lead to a massive protein damage and necrotic death, the anti-aggregating and protein refolding activities of Hsp72 may indeed become critical for cell protection. On the other hand, upon exposure to stresses that lead to apoptosis, the protective function of Hsp72 could be fully accounted for by its distinct role in cell signaling. Under these conditions, protein damage on its own is not sufficient for cell death because suppression of the apoptotic signaling pathway restores cell viability. Indeed, specific inactivation of a stress-kinase JNK, an essential element of this signaling pathway, prevents stress-induced apoptosis. This was demonstrated by interruption of JNK signaling pathway either immediately upstream of JNK (by expression of dominant-negative mutants of JNK activator SEK1) or immediately downstream of JNK (by expression of a dominant negative mutant of c-jun). Recently it was demonstrated that the distinct role of Hsp72 in protection of cells from heat-induced apoptosis is, in fact, suppression of JNK activation. A greater understanding of the role of Hsp72 in aged cells could have important therapeutic applications.

SUMMARY OF THE INVENTION

The present invention relates, in one aspect, to a method for inducing Hsp72 production in a cell. The method involves contacting the cell transiently with a proteasome inhibitor in an amount sufficient to induce Hsp72 production. Preferably Hsp72 levels are induced to a level sufficient for the suppression of stress-activated kinase activity attributable, for example, to a stress-activated kinase selected from the group consisting of JNK and p38. The method has both in vitro and in vivo applications. In a second embodiment, a method of the type described above is applied specifically to aged cells. Aged cells are known to exhibit decreased ability to express Hsp72 in response to stress.

In another embodiment, the present invention relates to a method for treating pathologies associated with apoptosis and inflammation in an individual. The method involves administering to the individual a proteasome inhibitor in an amount sufficient to induce Hsp72 production. In a preferred embodiment of the therapeutic method, the individual is an aged individual. Stress-induced pathologies such as ischemia are particularly important with respect to the therapeutic aspect of the invention.

In another embodiment, the present invention relates to a method for identifying an organic compound having the ability to induce Hsp72 levels in aged cells to a level sufficient to suppress stress-activated kinase activity. The method involves contacting aged cells in culture with a candidate organic compound, determining an increase in Hsp72 levels in the aged cells in culture and correlating an increase in Hsp72 levels with the suppression of stress-activated kinase activity.

DETAILED DESCRIPTION OF THE INVENTION

The present invention is based on the discovery that Hsp72 induction can protect a cell against apoptosis by inhibiting the activity of stress kinase proteins. More specifically, as reported in the Exemplification section which follows, it was discovered that the activity of the stress kinase proteins JNK and p38 were inhibited by Hsp72.

Thus, in one aspect, the present invention relates to a method for inducing Hsp72 expression. Induction of Hsp72 is effected in non-aged cells through the transient administration of a proteasome inhibitor. By way of background, an ATP-dependent soluble proteolytic pathway which is operational in the cytosol requires the covalent conjugation of ubiquitin to a target protein. Following attachment of ubiquitin to the target protein, the conjugate is hydrolyzed by a 26S proteolytic complex which contains a 20S degradative particle called the proteasome. The proteasome is known to be responsible for the hydrolysis of abnormal proteins and short-lived regulatory proteins (e.g., transcription factors).

The proteasome is composed of about 15 distinct subunits of about 20–30 kDa each. These include a set of 3–4 peptidases which specifically cleave on the carboxyl side of the hydrophobic, basic, and acidic amino acids. The peptidases responsible for these cleavage activities are referred to as the chymotrypsin-like peptidase, the trypsin-like peptidase and the peptidylglutamyl-like peptidase, respectively.

A variety of inhibitors of the proteasome complex have been reported in the literature (see e.g., Dick et al., *Biochem.* 30: 2725 (1991); Goldberg et al., *Nature* 357: 375 (1992); Goldberg, *Eur. J. Biochem.* 203: 9 (1992); Orlowski, *Biochem.* 29: 10289 (1989); Rivett et al., *Archs. Biochem. Biophys.* 218: 1 (1989); Rivett et al., *J. Biol. Chem.* 264: 12,215 (1989); Tanaka et al., *New Biol.* 4: 1 (1992)). Proteasome inhibitors are also discussed in U.S. Pat. No. 5,693,617, the disclosure of which is incorporated herein by reference.

These proteasome inhibitors include specific inhibitors of the peptidases of the proteasome. More specifically, these inhibitors of the peptidases of the proteasome include inhibitors of the chymotrypsin-like and trypsin-like proteases, in addition to thiol and serine proteases. In addition to antibiotic inhibitors originally isolated from actinomycetes, a variety of peptide aldehydes have been synthesized, such as the inhibitors of chymotrypsin-like proteases described by Siman et al. (WO91/13904).

In addition to the known proteasome inhibitors, other molecules can also be routinely tested for their ability to inhibit the proteasome activity. Various strategies for the identification of such inhibitors are exemplified in the citations referred to in the preceding paragraphs. Small molecule libraries, often comprising extracts from plants or more simple organisms, may be screened for their ability to inhibit specific protease types. Alternatively, a rational design approach may be applied using, for example, peptide or peptidomimetic compounds designed specifically to interact with the active site of a proteasome component (see e.g., Siman et al., WO91/13904; Powers et al., in *Proteinase Inhibitors*, Barrett et al. (eds.), Elsevier, pp. 55–152 (1986)). The inhibitors can be stable analogs of catalytic transition states such as Z-Gly-Gly-Leu-H, which inhibits the chymotrypsin-like activity of the proteasome (Orlowski, *Biochemistry* 29: 10289 (1990); see also Kennedy and Schultz, *Biochem.* 18: 349 (1979)).

A variety of natural and chemical protease inhibitors reported in the literature, or analogs thereof, include peptides containing an α-diketone or an α-ketone ester, peptide chloromethyl ketone, isocoumarins, peptide sulfonyl fluorides, peptidyl boronates, peptide epoxides, and peptidyl diazomethanes. Angelastro et al., *J. Med. Chem.* 33: 11 (1990); Bey et al., EPO 363,284; Bey et al., EPO 363,284; Bey et al., EPO 364,344; Grubb et al., WO 88/10266; Higuchi et al., EPO 393,457; Ewoldt et al., *Mol. Immunol.* 29(6): 713 (1992); Hernandez et al., *J. Med. Chem.* 35(6): 1121 (1992); Vlasak et al., *J. Virol.* 63(5): 2056 (1989); Hudig et al., *J. Immunol.* 147(4): 1360 (1991); Odakc et al., *Biochem.* 30(8): 2217 (1991); Vijayalakshmi et al., *Biochem.* 30(8): 2175 (1991); Kam et al., *Thrombosis and Haemostasis* 64(1): 133 (1990); Powers et al., *J. Cell. Biochem.* 39(1): 33 (1989); Powers et al., *Proteinase Inhibitors*, Barrett et al., Eds., Elsevier, pp. 55–152 (1986); Powers et al., *Biochem* 29(12): 3108 (1990); Oweida et al., *Thrombosis Res.* 58(2): 391 (1990); Hudig et al., *Mol. Immunol.* 26(8): 793 (1989); Orlowski et al., *Arch. Biochem. and Biophys.* 269(1): 125 (1989); Zunino et al., *Biochem. et Biophys. Acta* 967(3): 331 (1988); Kam et al., *Biochem.* 27(7): 2547 (1988); Parkes et al., *Biochem. J.* 230: 509 (1985); Green et al., *J. Biol. Chem.* 256: 1923 (1981); Angliker et al., *Biochem. J.* 241: 871 (1987); Puri et al., *Arch. Biochem. Biophys.* 27: 346 (1989); Hanada et al., *Proteinase Inhibitors: Medical and Biological Aspects*, Katunuma et al., Eds., Springer-Verlag pp. 25–36 (1983); Kajiwara et al., *Biochem. Int.* 15: 935 (1987); Rao et al., *Thromb. Res.* 47: 635 (1987); Tsujinaka et al., *Biochem. Biophys. Res. Commun.* 153: 1201 (1988)).

Certain peptide aldehydes and peptide α-keto esters containing a hydrophobic residue in the $P_1$ position were tested by Vinitsky et al. (Biochem. 31: 9421 (1992), see also Orlowski et al., Biochem. 32: 1563 (1993)) as potential inhibitors of the chymotrypsin-like activity of the proteasome. three peptide aldehydes, (benzyloxycarbonyl)-Leu-Leu-phenylalaninal (Z-LLF-H), N-acetyl-Leu-Leu-methioninal (Ac-LLM-H), and N-acetyl-Leu-Leu-methioninal (Ac-LLM-H) were found to be slow binding inhibitors with $K_i$ values of 0.46, 5.7, and 33 uM, respectively. Of the several peptide α-keto ester inhibitors tested, Z-Leu-Leu-Phe-COOEt was the most potent inhibitor of the chymotrypsin-like activity with a $K_i$ of 53 uM.

Other tripeptides that have been described in the literature include Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H and Z-Arg-Ile-Phe-H, where OR, along with the carbonyl of the preceding amino acid residue, represents an ester group.

Tsubuki et al., *Biochem. and Biophys. Res. Commun.* 196(3): 1195 (1993) reported features of a tripeptide aldehyde protease inhibitor, benzyloxycarbonly(Z)-Leu-Leu-Leu-H. The following synthetic peptides are also mentioned: Z-Leu-Leu-Gly-H, Z-Leu-Leu-Ala-H, Z-Leu-Leu-Ile-H, Z-Leu-Leu-Val-H, Z-Leu-Leu-Nva-H, Z-Leu-Leu-Phe-H, Z-Leu-Leu-Leu-H, Bz-Leu-Leu-Leu-H, Ac-Leu-Le-Leu-H, Z-Leu-Leu-Leu.sc, Z-Leu-Leu-Leu.ol, Z-Leu-Leu-Leu, Dns-Leu-Leu-Leu-H, Dns-Leu-Leu-Leu-CH$_2$Cl and leupeptin.

Siman et al. (WO 01/13904) disclose chymotrypsin-like proteases and their inhibitors. The inhibitors have the formula R-A4-A3-A2-Y, wherein R is hydrogen, or an N-terminal blocking group; A4 is a covalent bond, an amino acid or a peptide; A3 is a covalent bond, a D-amino acid, Phe, Tyr, Val or a conservative amino acid substituent of Val; A2 is a hydrophobic amino acid or lysine or a conservative amino acid substituent thereof, or when A4 includes at least two amino acids, A2 is any amino acid; and Y is a group reactive with the active site of said protease.

Powers (WO 92/12140) discloses peptide ketoamides, ketoacids, and ketoesters and their use in inhibiting serine proteases and cysteine proteases. Bartus et al. (WO 92/1850) disclose uses for calpain inhibitor compounds and pharmaceutical compositions containing them.

A preferred class of proteasome inhibitor is the peptide aldehyde class. These inhibitors bind to the proteasome noncovalently, although with high affinity, and can easily dissociate having a high rate of off-reaction. These properties provide the ability of peptide aldehydes to induce Hsp72 efficiently at low concentrations while having low toxicity in comparison with other classes of inhibitors. A representative of this class of proteasome inhibitor which was used in connection with the experiments described below is MG132. It is well-known to those of skill in the art that MG132, like other proteasome inhibitors, is a toxic compound. Most cells which are treated non-transiently with a proteasome inhibitor are committed to an apoptotic death.

In one aspect, the present invention relates to Applicants' discovery that transient exposure of a cell to a proteasome inhibitor can be sufficient to induce Hsp72 expression, while not committing the cell to apoptotic death. Transient exposure, as that expression is used herein, refers to exposure conditions which must necessarily be determined empirically in light of the fact that not all proteasome inhibitors exhibit identical potencies, and not all cell types respond to the same proteasome inhibitor in an identical manner. Within the context of the present invention, transient exposure is defined as exposure of a cell to a proteasome inhibitor at a sufficient concentration and for a period of time sufficient to induce Hsp72 expression to levels sufficient for the suppression of stress-activated kinase activity. For the purposes of determining whether a particular exposure satisfies this definition, JNK and/or p38 activity may be measured using conventional techniques.

The methods of the present invention find application both in vivo and in vitro. An important in vitro application relates to the preservation of organs removed from a donor prior to transplant in a recipient. Such organs are in a stressed state due, for example, to decreased oxygen perfusion. Stress-activated kinases such as JNK are induced in an apoptotic cascade which leads to programmed cell death. Clearly it is desirable to limit tissue death in the organ prior to transplant. By incubating the organ transiently in a solution containing a proteasome inhibitor, Hsp72 can be induced to a level sufficient to suppress activation of stress-activated kinases.

Initial steps in protocol development for a given proteasome inhibitor are established using organs from animal model donor. The proteasome inhibitor of interest is administered in varying concentration for predetermined periods of time. The animal model donor organ is then tested for stress-activated kinase activity in vitro. When Hsp72 levels have been sufficiently induced, the organ is washed to remove the proteasome inhibitor. In doing so, prolonged exposure to the proteasome inhibitor, which generally leads to apoptosis, is avoided.

Similar in vivo utilities are encompassed by the scope of the present invention. In vivo, stresses result in both apoptosis and inflammatory responses. The stress-activated kinase JNK participates in the apoptotic cascade whereas p38 has been determined to participate in the inflammatory processes. Stress-induced pathologies include those characterized by an imbalance between oxygen supply and demand. The ischemias are included within this class of pathology.

Consider, for example, the pathology of stroke. In the United States it has been estimated that more than 400,000 patients are discharged from hospitals each year following treatment for stroke. Approximately 80% of strokes are due to ischemic cerebral infarction. Within hours to days, the gray matter of the brain becomes congested with engorged, dilated blood vessels and minute petechial hemorrhages. Subsequent recirculation into the ischemic area following, for example, migration or lysis of a blockage, causes hemorrhagic infarction that may aggravate edema formation from blood-brain barrier disruption. A primary intracerebral hemorrhage damages the brain directly at the site of the hemorrhage by compressing the surrounding tissue.

The brain is unable to repair itself and forms scar tissue at the site of infarction or hemorrhage. Following a stroke, therapy is directed toward minimizing subsequent worsening of the infarction or hemorrhage, preventing a second stroke or decreasing edema. The transient, intravenous administration of a proteasome inhibitor following stroke will minimize permanent and irreversible damage to the brain tissue. Transient administration in an in vivo context is achieved through the administration of a proteasome inhibitor having a relatively short half-life. The turnover rate of the proteasome inhibitor could be determined in vivo by standard pharmacokinetic methods. As a test for the presence of such inhibitors in blood and other tissues, the ability of extracts to inhibit purified proteasome could be used.

Similar methods of therapeutic intervention are indicated, for example, in connection with ischemic acute renal failure (ARF), intestinal ischemia and ischemic heart disease. Ischemic ARF is frequently associated with apoptotic necrosis of tubule endothelial cells. Ischemic ARF occurs most frequently following primary stresses including cardiovascular surgery, trauma, hemorrhage, sepsis or dehydration. The intravenous administration of a proteasome inhibitor as treatment of a primary stress of this type will aid in the prevention of the secondary renal ischemic event.

Mesenteric or intestinal ischemia may be classified as occlusive or nonocclusive. Occlusion may result from arterial thrombus or embolus of the celiac or superior mesenteric arteries. Acute mesenteric ischemia is a very serious condition with high morbidity and mortality. Restoration of normal circulation may allow complete recovery if performed before irreversible apoptotic necrosis has occurred. Thus, in this context, the therapeutic transient administration of a proteasome inhibitor can prevent the triggering of the apoptotic program in mesenteric cells, thereby forestalling necrotic damage and providing a critical window for surgical intervention.

With respect to the heart, the most common cause of myocardial ischemia is atherosclerotic disease of epicardial coronary arteries. Reduction of the vessel lumen results in decreased myocardial perfusion. The abrupt development of ischemia typically affects the left ventricular myocardium resulting in failure of normal muscle contraction and relaxation. A prolonged ischemic event can lead to myocardial necrosis and scarring with, or without, clinical presentation of acute myocardial infarction. The transient administration of a proteasome inhibitor during such an event can minimize apoptotic necrosis while providing a therapeutic window for surgical intervention, for example.

In addition to treatment of apoptotic pathologies of the type described above, transient administration of proteasome inhibitors is also indicated in connection with acute inflammatory disorders. Adult respiratory distress syndrome (ADRS) is an acute pulmonary inflammation which often follows the generalized sepsis and other inflammatory conditions. It develops in a large fraction of individuals with sepsis within several hours to days after the initial detection of infection in the blood. The prognosis of ADRS is poor with a mortality rate of about 50%. The major cause of the disease is an excessive synthesis and release of proinflammatory cytokines in lungs in response to endotoxin. In a mouse model, the ADRS stimulated by endotoxin shock can be efficiently suppressed by the mild heating of the whole mouse, which induces Hsp72. These data strongly suggest that induction of Hsp72 is an effective therapeutic approach in humans as well. To achieve induction of Hsp72, proteasome inhibitors could be administrated either IV or directly into lungs in the form of an aerosol. This could be done prophylactically immediately following the detection of bacteria in blood. Several hours before development of ADRS will be sufficient for lung cells to accumulate Hsp70 and suppress ADRS.

The discussion set forth above relates to cells regardless of their aged status. In another aspect, the present invention relates to a method for inducing Hsp72 expression in aged cells. In preferred embodiments, Hsp72 is induced to levels sufficient to suppress stress-activated kinase activity. The cells of an aged organism contain very low levels of Hsp72 and there are no known inducers of Hsp72 which are useful in aged cells.

As shown in the experiments described below, it was determined that MG132 could be used to induce Hsp72 in aged cells. In fact, it was determined that Hsp72 could be induced to a level sufficient to prevent the activation of stress kinases. This Hsp72-mediated suppression of stress kinase activity can block cellular apoptosis in aged cells.

Aged cells are typically defined on the basis of the number of cell divisions undergone. In this sense, the definition is species-specific. For examples, in humans an aged cell can be considered to be at late 50th and more divisions in culture. Although the number of divisions the cell can pass in the organism is higher, cells aged in culture possess the same physiological properties as cells isolated from the aged organism. For example, both have prolonged cell cycles, both are unable to induce heat shock proteins, etc. Therefore, cells aged in culture provide an adequate biochemical model of aging.

The therapeutic methods described above in connection with non-aged cells are also applicable to the cells of an aged organism. In fact, therapeutic application in an aged organism is likely to be the more significant context given the fact that Hsp72 levels are known to be low in aged cells. Prior to the work described herein, it was not known that Hsp72 production was inducible in aged cells.

In another aspect, the present invention relates to methods for identifying a compound characterized by the ability to induce Hsp72 expression in aged cells. Such a method is clearly applicable to the identification of members of the proteasome inhibitor class of organic compounds which possess this ability. However, the methods can be applied to the screening of any type of organic compound for the ability to induce Hsp72. Pharmaceutical companies maintain large libraries of candidate compounds for screening. Many of these candidate compounds are isolated from plant or fungal extracts, for example. The screening method is exemplified below and involves contacting experimental cells in vitro with a candidate organic compound and determining the ability of the candidate compound to induce Hsp72 expression in the aged cell. Preferably, the identified compounds have the ability to induce Hsp72 to a level sufficient to suppress stress- activated kinase activity.

EXEMPLIFICATION

EXAMPLE 1

REDUCED THERMOTOLERANCE IN AGED CELLS RESULTS FROM LOSS OF THE HSP72-MEDIATED CONTROL OF JNK SIGNALING PATHWAY

Experiments reported in this Example were designed to test the hypotheses, that because of the diminished inducibility of Hsp72 in aged cells, Hsp72-mediated control of JNK in response to heat shock is compromised, resulting in a higher rate of apoptosis and thus in reduced resistance to hyperthermia.

Material and Methods i) Experimental Procedures Cell Line and Materials

Human lung fibroblasts IMR90 which underwent either 12–17 divisions ("young" cells) or 62–67 divisions ("old" cells) were grown in MEM medium supplemented with 20% bovine fetal serum and 2mM glutamine. The cells were seeded at a density of 1.105 cells/35 mm plate and grown at 37° C. in an atmosphere of 95% air and 5% $CO_2$. Cultures were split when cell density reached confluency. MG132 was purchased from Biomol Res Lab, Inc, PA. Anti-Hsp72 antibody (SPA810) was from StressGene Biotechnologies Corp (Canada).

ii) Adenovirus-based expression of Hsp72

Recombinant adenovirus vector expressing Hsp72 (ADTR5Hsp72-GFP) was constructed by cloning a dicistronic transcription unit encoding Hsp72 and Aequorea Victoria green fluorescent protein gene, separated by the encephalomyocarditis virus internal ribosome entry site from pTR-DC/HSP70-GFP (Mosser et al., *Molecular & Cellular Biology* 17: 5317–27 (1997); Mosser et al., *Biotechniques* 22: 150–4, 156, 158–61 (1997)), into an adenovirus transfer vector. Expression of this transcription unit is controlled by the tetracycline-regulated transactivator protein tTA (Mosser et al., *Biotechniques* 22: 150–4, 156, 158–61 (1997)) which were expressed from a separate recombinant adenovirus. Recombinant adenoviruses were generated by standard techniques as detailed by Jani et al. (*Journal of Virological Methods* 64: 111–24 (1997)). Viruses were used at stock concentration of 1010 pfu/ml. Infection of cells with both viruses simultaneously led to expression of Hsp72 in the absence of tetracycline but not in the presence of 20 nM of anhydrotetracyclin. Two-ml cell cultures grown in 35 mm dishes were infected in the presence or the absence of anhydrotetracyclin with 3.107 pfu of each virus, sufficient for infection of almost 100% cells. After 3 hours incubation with viruses, cells were washed with PBS and placed in fresh media with or without anhydrotetracyclin.

iii) Treatment of cells with MG132

Young and old cells were incubated with either 1 or 2 mM of MG132 for 5 hours, washed with PBS and incubated in a fresh medium for an additional 12 hours.

iv) JNK assay

JNK activity was assayed using GST-c-Jun protein as a substrate after immunoprecipitation with anti-JNK1 antibodies (sc-474, Santa Cruz Biotechnology, Inc., CA). Briefly, cells were lysed in a buffer containing 20 mm Tris-HCl, pH 7.4, 50 mm NaCl, 2 mm EDTA, 1% Triton X-100, 25 mm b-glycerophosphate, 10 mm NaF, 1 mm Na3VO4, and protease inhibitors (1 mm PMSF and 25 mg/ml each of aprotenin, pepstatin, leupeptin). After immunoprecipitation with anti-JNK1 antibody and protein A-sepharose for 2 h at 4° C. and washing, kinase reaction was carried out in a buffer containing 25 mm HEPES, 10 mm MgCl2, 2 mm DTT, 25 mm b-glycerophosphate, 2 mm Na3VO4 and 25 mCi 32P-g-ATP at 37° C. for 10 min. Then the samples were subjected to SDS-PAGE followed by transfer to a nitrocellulose membrane and autoradiography. This membrane was later used for immunoblot with anti-JNK1 antibody to ensure that equal amounts of the kinase were immunoprecipitated.

v) Detection of heat-induced apoptosis

Young and old cells were subjected to heat shock at 45° C. for different time periods followed by incubation at 37° C. After 24 hours cells were stained with Hoechst 33342 according to manufacturer's specifications.

Results

To test the hypothesis that because of the diminished inducibility of Hsp72, aged cells are deficient in Hsp72-mediated control of JNK in response to heat shock, human lung fibroblasts IMR90 were used. Cells which passed 62–67 divisions were designated "old cells" and cells of the same origin (same isolation) which passed only 12–17 divisions were designated "young cells". Heat shock of various severity (43° C. for 30 min, 43° C. for 60 min, 450° C. for 30 min and 45° C. for 75 min.) caused strong activation of JNK to levels similar in both young and old cells. In a parallel experiment the same heat shock was preceded by incubation at 43° C. for 30 min (mild heat shock which caused only a weak transient activation of JNK in both young and old cells) followed by a 6 hours recovery at normal temperature. This pretreatment led to substantial accumulation of Hsp72 in young but not in old cells during the recovery period.

Pretreatment with a mild heat shock suppressed activation of JNK by the second heat shock in young but not in old cells. In these experiments strong activation of JNK by heat shock in aged cells correlated with the decline in the inducibility of Hsp72, suggesting a possible causal relationship. Two major components contribute to cell's resistance to hyperthermia—intrinsic tolerance and acquired thermotolerance, which results from induction of Hsps after mild heat shock. The results described above show that without pretreatment with a mild heat shock the extent of JNK activation was similar in young and old cells, suggesting that intrinsic tolerance (or rather sensitivity) would also be similar. In contrast, pretreatment with a mild heat shock leads to acquisition of the ability to suppress JNK activation only by young but not old cells, suggesting that acquired thermotolerance would be very different.

To evaluate intrinsic tolerance, cells were subjected to severe heat shock (45° C. for different time periods), and the proportion of dying cells was measured 24 hours later. The vast majority of the dying cells exhibited typical signs of apoptosis including cell shrinkage and nuclear condensation, while the integrity of the cell membrane was unaffected. As seen in Table 1, intrinsic tolerance in young and old cells was essentially identical. To evaluate an acquired thermotolerance, severe heat shock was preceded by a mild heat shock at 43° C. for 30 min. followed by a 6 hour recovery to allow accumulation of Hsps. As seen in Table 1, the acquired thermotolerance in young and old cells was dramatically different, i.e. pretreatment with mild heat shock strongly increased survival of young cells and did not affect the viability of old cells. These observations are consistent with the notion that the inability of old cells to establish Hsp72-mediated control of JNK leads to their inability to acquire thermotolerance.

Thus, it would be of interest to determine whether the diminished ability to express Hsp72, rather than other physiological changes associated with aging, is primarily responsible for uncontrolled JNK activation in old cells. To answer this question, an adenovirus-based construct that expresses Hsp72 under the control of a tetracycline-inhibitable transactivator was used. Infection of both young and old cells resulted in expression of Hsp72 in essentially all cells in the absence but not in the presence of tetracycline. Within 36 hours, Hsp72 accumulated to the levels comparable with those achieved after pretreatment of young cells with mild heat shock. When severe heat shock was administered 36 hours after infection, suppression of JNK activation and protection from apoptosis were evident in both young and old cells; neither effect was observed when cells (both young and old) were infected and maintained in the presence of tetracycline. Therefore, defects in the control of JNK and consequently reduced resistance to hyperthermia in old cells are caused indeed by the deficiency in induction of Hsp72.

Induction of Hsp72 would clearly be of high therapeutic value (Biro et al., *Brain Research Bulletin* 44: 259–263 (1997); Vigh et al., *Nature Medicine* 3: 1150–1154 (1997)), especially in old organisms, because Hsp72 protects not only from hyperthermia but also from a variety of pathological conditions such as heart ischemia (Mestril et al., *Journal of Molecular & Cellular Cardiology* 28: 2351–8 (1996); Hutter et al., *Circulation* 94: 1408–11 (1996); Morris et al., *Journal of Clinical Investigation* 97: 706–12 (1996); Dillmann, W. H., and Mestril, R., *Zeitschrift fur Kardiologie* 84(Suppl 4): 87–90 (1995)), stroke (Kabakov, A., and Gabai, V., *Heat Shock Proteins and Cytoprotection: ATP-deprived mammalian cells*. Molecular Biology Intelligence Unit, R.G.Landes Company, Austin (1997)), and others.

The results presented above show that it is possible to achieve forced exogenous virus-based expression of Hsp72 in old cells, but for obvious reasons it would be very desirable to find a way to induce endogenous Hsp72. However, all tested Hsp72-inducing stimuli, such as heat shock, mitogens (Faassen et al., *Experimental Cell Research* 183: 326–34 (1989)), canavanine (Liu et al., *Journal of Biological Chemistry* 264: 12037–45 (1989)), arsenite (Luce, M. C., and Cristofalo, V. J., *Experimental Cell Research* 202: 9–16 (1992)), restrain stress (Udelsman et al., *Journal of Clinical Investigation* 91: 465–73 (1993)) and others, failed to restore expression of Hsp72 in aged cells.

In these experiments, a proteasome inhibitor (MG132) which induces Hsp72 in various cell lines was tested to determine whether it could activate Hsp72 expression in old cells. The rational for these experiments was based on the fact that induction of Hsp72 in response to heat shock is mediated by the Heat Shock Transcription Factor 1 (HSF1) (Morimoto et al., *Stress-Inducible Cellular Responses* (Feige et al., ed)^eds) 77: 139–63, Birkhauser Verlag, Basel (1996); Voellmy, R., *Stress-Inducible Cellular Responses* (Feige et al., ed)^eds) 77: 121–37, Birkhauser Verlag, Basel (1996)). In old cells, however, activation of HSF1 is compromised, thus resulting in diminished inducibility of Hsp72 (Heydari et al., *Experientia* 50: 1092–8 (1994); Heydari et al., *Molecular and Cellular Biology* 15: 2909–2918 (1993)). In addition to HSF1, at least two other HSFs (HSF2 and HSF3) are present in mammalian cells (Sistonen et al., *Molecular & Cellular Biology* 14: 2087–99 (1994); Tanabe et al., *Journal of Biological Chemistry* 272: 15389–95 (1997); Nakai et al., *Molecular & Cellular Biology* 15: 5268–78 (1995)), but their role in expression of Hsp72 is poorly understood. A recent observation indicates that a proteasome inhibitor MG132 induces Hsp72 not only via HSF1 (Zhou et al., *Journal of Biological Chemistry* 271: 24769–24775 (1996)), but also HSF2. Such MG132-mediated induction of Hsp72 is sufficient to suppress JNK activation in response to heat shock in several cell lines.

Since no deficiency in HSF2 function was reported in old cells, MG132 was tested to determine whether it could be used with old cells as an inducer of Hsp72 in order to suppress JNK activation. The experiments demonstrated that while the capability of old cells to express Hsp72 in response to heat shock was compromised, synthesis of this heat shock protein upon incubation with MG132 was similar in old and young cells. Hsp72s levels induced by MG132 exceeded those triggered in young cells by a mild heat shock employed in this study. When cells pretreated with MG132 were subjected to heat shock of various severity, JNK activation was strongly suppressed in both young and old cells, and consequently both were protected from apoptosis. These data demonstrate for the first time that old cells retain the capability to express Hsp72 at the levels similar to those of young cells. Furthermore, induction of Hsp72 by alternative methods can interfere with JNK signaling pathway and reduce thermosensitivity in old cells.

These results thus confirm the hypothesis that lack of the Hsp72-mediated control of JNK in old cells is at the basis of their increased thermosensitivity. Indeed, it appears that Hsp72 is both necessary and sufficient for restoration of aged cell's ability to control JNK activation.

TABLE 1

Intrinsic and acquired thermotolerance in old and young cells.

| Cells | Preheating | Incubation at 45° C., min. | | | |
|---|---|---|---|---|---|
| | | 0 | 40 | 55 | 75 |
| Young | − | 1.4 + 1.2 | 2.6 + 1.2 | 15.4 + 2.4 | 80.0 + 7.9 |
| Young | + | 1.2 + 1.0 | 1.2 + 1.0 | 4.0 + 3.7 | 18.0 + 4.0 |
| Old | − | 2.0 + 2.0 | 3.0 + 2.6 | 12.0 + 2.9 | 76.0 + 7.9 |
| Old | + | 2.1 + 1.9 | 3.0 + 2.6 | 14.0 + 4.0 | 78.0 + 8.9 |

Young and old cells were subjected to heat shock at 45° C. for 40, 55 or 75 min. with or without pretreatment with mild heat shock at 43° C. for 30 min. followed by 6 hours recovery at 37° C. After 24 hours cells, grown on slides, were stained with combination of Hoechst 33342 and ethidium bromide, and the proportion of apoptotic cells was determined under fluorescent microscope.

EXAMPLE 2

PROTEASOME INHIBITORS PROTECT CELLS FROM APOPTOSIS BY INDUCING Hsp72 AND SUPPRESSING STRESS-KINASE JNK

Materials and Methods i) cells and reagents

U937 human lymphoid tumor cells were grown in RPMI-1640 medium with 10% fetal bovine serum and were used for experiments while in the mid log-phase (3–7.105 cells/ml). 293 human cells were grown in DMEM medium with 10% fetal bovine serum and were used in transient transfection experiments while at 40% of confluence. MG132 was purchased from Biomol Res Lab, Inc, PA. aLLN was purchased from Sigma, MO. MG132 analogs were synthesized and purified by HPLC. Anti-hsp72 antibody (SPA810) was from StressGene Biotechnologies Corp (Canada), anti-p53 antibody (PAb1801) was from SantaCruz Biotechnology, Inc, Calif.

ii) JNK and p38 assay

JNK activity was assayed using GST-c-Jun protein as a substrate after immunoprecipitation with anti-JNK1 antibodies (sc-474, Santa Cruz Biotechnology, Inc., Calif.), or anti-HA antibody for transfected JNK (Berkley Antibody Company). Briefly, cells were lysed in a buffer containing 20 mM Tris-HCl, pH 7.4, 50 mM NaCl, 2 mM EDTA, 1% Triton X-100, 25 mM b-glycerophosphate, 10 mM NaF, 1 mM Na3VO4, and protease inhibitors (1 mM PMSF and 25 mg/ml each of aprotenin, pepstatin, leupeptin). After immunoprecipitation with anti-JNK1 or anti-HA antibody and protein A-sepharose for 2 h at 4° C. and washing, kinase reaction was carried out in a buffer containing 25 mM HEPES, 10 mM $MgCl_2$, 2 mM DTT, 25 mM b-glycerophosphate, 2 mM $Na_3VO_4$ and 25 mCi 32P-g-ATP at 37° C. for 10 min. Samples were then subjected to SDS-PAGE followed by transfer to a nitrocellulose membrane and autoradiography. This membrane was later used for immunoblot with anti-JNK1 antibody to ensure that equal amounts of the kinase were immunoprecipitated. p38 kinase activity was determined by Western blot with polyclonal antibody (New England Biolabs, MA) specifically recognizing the phosphorylated (active) form of p38. Later the same blot was treated with anti-p38 antibody (New England Biolabs, Mass.) to assure equal loading of the kinase on different lanes.

iii) apoptosis assays

PARP degradation was followed by Western blotting with anti-PARP monoclonal antibodies (C2-10, G. Poirier, Montreal, Canada). Apoptosis of 293 cells was detected by cleavage of a truncated form of Ul-70 kDa protein d12 (Romac, J. M. J. et al., *Mol Cell Biol* 14: 4662–4670 (1994)). Cells were transfected by calcium phosphate method with a plasmid encoding d12 tagged with T7 epitope alone or together with a dominant-negative mutant forms of SEK1 (K/R) or c-jun (TAM67). After 48 hours cells were either treated with 10 mM MG132 or subjected to heat shock at 45° C. for 15 min. After additional 24 hours cells were lysed and cleavage of d12 was detected by Western blot with anti-T7 epitope antibody.

Results i) Anti-apoptotic effects of the proteasome inhibitors

Experiments were designed to determine the nature of anti-apoptotic action of the inhibitors. It was previously described that exposure to proteasome inhibitors induces 70 kDa heat shock protein, Hsp72 (Bush, K. T. et al., *J Biol Chem* 272: 9086–9092 (1997); Zhou, M. et al., *J Biol Chem* 271: 24769–24775 (1996)). Recently it was reported that Hsp72 accumulation confers resistance to apoptosis (Gabai, V. L. et al., *J Biol Chem* 272: 18033–18037 (1997); Simon, M. M. et al., *J Clin Invest* 95: 926–933 (1995); Samali, A. and Cotter, T., *Exp Cell Res* 223: 163–170 (1996); Gabai, V. L. et al., *FEBS Lett* 375: 21–26 (1995); Mosser, D. D. and Martin, L. H., *J Cell Physiol* 151: 561–570 (1992)) .

In the experiments described herein, incubation of U937 cells with MG132, lactacystin-β-lacton, NIP-L3VS or aLLN was found to dramatically increase the levels of Hsp72. Hsp40 and Hsp27 also appeared to be induced by incubation with MG132. By contrast, treatment with even high concentrations of less active and inactive MG132 analogs, Z-LLL, Z-LLN or Z-LLL-amide did not lead to any significant induction of Hsp72. This data indicate that induction of Hsp72 was caused by inhibition of the proteasome-dependent protein breakdown. To investigate whether the induction of Hsp72 by proteasome inhibitors leads to suppression of apoptosis caused by certain stresses, a search was designed to determine conditions under which anti-apoptotic action of proteasome inhibitors could be separated from their pro-apoptotic effect. Incubation of cells with 1.5 mM of MG132 for 4.5 hours, followed by its withdrawal from the culture, activated JNK only temporally, which was insufficient to induce apoptosis. This treatment, on the other hand, was sufficient to cause strong accumulation of Hsp72 after several hours of recovery. These conditions appeared to be suitable for revealing an anti-apoptotic action of the proteasome inhibitor. Using heat shock as an apoptotic stimulus, it was determined that pretreatment with MG132 reduced the extent of cell death from about 40% to a negligible level. Thus, while long incubation of U937 cells with the proteasome inhibitor caused prolonged activation of JNK leading to apoptosis, by contrast, short incubation of the same cells with this inhibitor caused temporal nontoxic activation of JNK and induction of Hsp72, which protected cells from certain stresses.

Experiments were designed to determine the mechanism of protection of cells from stresses after pretreatment with the proteasome inhibitors. It was previously observed that overproduction of Hsp72 blocks stress-induced apoptosis by suppression of JNK (Gabai, V. L. et al., *J Biol Chem* 272: 18033–18037 (1997)). In line with this data, MG132-induced protection of cells from heat shock also resulted from suppression of JNK. In fact, severe heat shock of pretreated cells led to much lesser activation of this kinase compared to activation of JNK under the same conditions in untreated cells.

The effects of preincubation of cells with MG132 on severe heat shock-induced JNK activation and apoptosis were indistinguishable from the effects of pretreatment with mild heat shock or overproduction of recombinant Hsp72 (Gabai, V. L. et al., *J Biol Chem* 272: 18033–18037 (1997)). Therefore, the protective effects of MG132 on cells apparently is due to the Hsp72-mediated suppression of JNK.

To further evaluate the suggestion whether pretreatment with MG132 prevents apoptosis by suppression of JNK, experiments were designed to test the effects of such pretreatment on two other types of apoptosis: ethanol-induced apoptosis, which requires JNK, and TNF-induced apoptosis, which is able to mobilize distinct, JNK-independent pathway (Liu, Z. et al., *Cell* 87: 565–576 (1996); Natoli, G. et al., *Science* 275: 200–203 (1997)). MG132 strongly suppressed activation of JNK by both ethanol and TNF, while effects on cell death were strikingly different. Similarly to its effects on heat shock-induced apoptosis, pretreatment with MG132 suppressed cell death caused by ethanol. By contrast, pretreatment with this inhibitor did not rescue cells from TNF-induced apoptosis and even potentiated it. Likewise, pretreatment of the cells with mild heat shock which induced Hsp72, strongly reduced activation of JNK after exposure to TNF, but no protection from TNF-induced apoptosis was observed under these conditions. Therefore, pretreatment with proteasome inhibitors appears to protect cells only from JNK-dependent apoptosis.

Discussion

Recently, proteasome inhibitors were demonstrated to cause very complex effects on programmed cell death. With some exceptions, it appeared that dividing cells respond to the inhibitors by activation of apoptosis, while in nondividing cells such inhibitors showed anti-apoptotic effects. Therefore, the common assumption was that this difference is attributed to difference in the cell types or in proliferating activity. Here it is demonstrated that both pro- and anti-apoptotic effects of proteasome inhibitors could be seen with the same cell line, U937, depending on the conditions of treatment, i.e. prolonged treatment resulted in apoptosis, while shorter exposure did not kill cells; it induced Hsp72 that caused protective effects.

Previously experiments demonstrated that overproduction of Hsp72 prevents apoptosis in response to a variety of stresses by suppression of activation of JNK (Gabai, V. L. et al., *J Biol Chem* 272: 18033–18037 (1997)). Accordingly, in this work MG132-induced accumulation of Hsp72 suppressed activation of JNK in response to severe heat shock and blocked apoptosis. These data suggested that the protective effect of the proteasome inhibitors is specific to the apoptotic pathway that involves JNK activation. By contrast, JNK-independent apoptosis was expected not to be sensitive to preincubation of cells with MG132. Although TNFA is a strong activator of JNK, TNFα-induced apoptosis was reported to be independent on JNK (Liu, Z. et al., *Cell* 87: 565–576 (1996); Natoli, G. et al., *Science* 275: 200–203 (1997)). Accordingly, it was observed that, pretreated with MG132 suppressed TNFα-activation of JNK, and did not reduce TNFα-induced apoptosis. Thus, the protective effects of the proteasome inhibitors indeed appeared to be limited to the JNK-dependent apoptotic pathway.

What is claimed is:

1. A method for inducing Hsp72 production in an aged cell, the method comprising contacting the aged cell transiently with a proteasome inhibitor in an amount sufficient to induce Hsp72 production.

2. The method of claim 1 wherein Hsp72 levels are induced to a level sufficient for the suppression of stress-activated kinase activity.

3. The method of claim 2 wherein the stress-activated kinase activity is attributable to a stress-activated kinase selected from the group consisting of JNK and p38.

4. The method of claim 2 wherein the cell is contacted with the proteasome inhibitor in vitro.

5. The method of claim 2 wherein the cell is contacted with the proteasome inhibitor in vivo.

6. The method of claim 5 wherein the proteasome inhibitor is introduced by intravenous administration.

7. The method of claim 2 wherein the proteasome inhibitor is a peptide aldehyde.

8. A method for treating pathologies associated with apoptosis and inflammation in an aged individual, the method comprising transiently administering to the aged individual a proteasome inhibitor in an amount sufficient to induce Hsp72 production.

9. The method of claim 8 wherein the Hsp72 levels are induced to a level sufficient for the suppression of stress-activated kinase activity.

10. The method of claim 8 wherein the stress-activated kinase activity is attributable to a stress-activated kinase selected from the group consisting of JNK and p38.

11. The method of claim 10 wherein the stress-induced pathologies are characterized by an imbalance between oxygen supply and demand.

12. The method of claim 11 wherein the ischemia is a stroke due to ischemic cerebral infarction.

13. The method of claim 11 wherein the ischemia is ischemic acute renal failure.

14. The method of claim 11 wherein the ischemia is intestinal ischemia.

15. The method of claim 11 wherein the ischemia is ischemic heart disease.

16. The method of claim 8 wherein the pathologies are stress-induced pathologies.

17. The method of claim 16 wherein the pathology is an ischemia.

18. The method of claim 8 wherein the proteasome inhibitor is a peptide aldehyde.

19. A method for identifying an organic compound having the ability to induce Hsp72 levels in aged cells to a level sufficient to suppress stress-activated kinase activity, the method comprising:
   a) contacting aged cells in culture with a candidate organic compound;
   b) determining an increase in Hsp72 levels in the aged cells in culture;
   c) correlating an increase in Hsp72 levels with the suppression of stress-activated kinase activity.

20. The method of claim 19 wherein the candidate organic compound is a proteasome inhibitor.

21. The method of claim 19 wherein the proteasome inhibitor is a peptide aldehyde.

* * * * *

UNITED STATES PATENT AND TRADEMARK OFFICE
CERTIFICATE OF CORRECTION

PATENT NO. : 6,096,711
DATED : August 1, 2000
INVENTOR(S) : Michael Sherman et al.

It is certified that error appears in the above-identified patent and that said Letters Patent is hereby corrected as shown below:

Title page,
Below Item [76] Inventors, insert the following:
-- [73] Assignee: Boston Biomedical Research Institute, Watertown, Mass. --.

Column 14,
After line 13 and before line 30, delete claims 11-18 and replace with claims 11-18 as shown below:

11. The method of Claim 10 wherein the stress-induced pathologies are characterized by an imbalance between oxygen supply and demand.

12. The method of Claim 11 wherein the ischemia is a stroke due to ischemic cerebral infarction.

13. The method of Claim 11 wherein the ischemia is ischemic acute renal failure.

14. The method of Claim 11 wherein the ischemia is intestinal ischemia.

15. The method of Claim 11 wherein the ischemia is ischemic heart disease.

16. The method of Claim 8 wherein the pathologies are stress-induced pathologies.

17. The method of Claim 16 wherein the pathology is an ischemia.

UNITED STATES PATENT AND TRADEMARK OFFICE
CERTIFICATE OF CORRECTION

PATENT NO. : 6,096,711
DATED : August 1, 2000
INVENTOR(S) : Michael Sherman et al.

It is certified that error appears in the above-identified patent and that said Letters Patent is hereby corrected as shown below:

18. The method of Claim 8 wherein the proteasome inhibitor is a peptide aldehyde.

Signed and Sealed this

Twenty-eighth Day of May, 2002

Attest:

JAMES E. ROGAN
Attesting Officer     Director of the United States Patent and Trademark Office

UNITED STATES PATENT AND TRADEMARK OFFICE
CERTIFICATE OF CORRECTION

| | | |
|---|---|---|
| PATENT NO. | : 6,096,711 | Page 1 of 1 |
| APPLICATION NO. | : 09/030297 | |
| DATED | : August 1, 2000 | |
| INVENTOR(S) | : Michael Sherman et al. | |

It is certified that error appears in the above-identified patent and that said Letters Patent is hereby corrected as shown below:

Column 1, line 1:

Please insert as the first paragraph on page 1 of the issued patent, the following Government Support paragraph:

GOVERNMENT SUPPORT
    This invention was made with Government support under contract number GM54138, awarded by the National Institute of Health. The Government has certain rights in the invention.

Signed and Sealed this

First Day of May, 2007

JON W. DUDAS
*Director of the United States Patent and Trademark Office*